United States Patent [19]
Nagano

[11] Patent Number: 5,912,384
[45] Date of Patent: Jun. 15, 1999

[54] COLOR-STABILIZED BASIC MONOMERS, PROCESS FOR PRODUCING THE SAME AND METHOD FOR HANDLING THE SAME

[75] Inventor: Hideaki Nagano, Himeji, Japan

[73] Assignee: Nippon Shokubai Co., Ltd., Osaka, Japan

[21] Appl. No.: 08/998,825

[22] Filed: Dec. 29, 1997

[30] Foreign Application Priority Data

Dec. 27, 1996 [JP] Japan .................................. 8-349786

[51] Int. Cl.⁶ .................................................. C07C 69/52
[52] U.S. Cl. .......................................... 560/222; 564/204
[58] Field of Search .............................. 560/222; 564/204

[56] References Cited

FOREIGN PATENT DOCUMENTS

| 144521 | 12/1978 | Japan . |
| 134053 | 5/1992 | Japan . |
| 169559 | 6/1992 | Japan . |

OTHER PUBLICATIONS

Database WPI, Section Ch, Week 8782, Derwent Pub. Ltd., & JP 62 126 167 (Nippon Shokubai Kagaku Kogyo Co Ltd), Jun. 8, 1987.
CA 72: 112707 1969.

*Primary Examiner*—Paul J. Killos
*Attorney, Agent, or Firm*—Sherman and Shalloway

[57] ABSTRACT

Color-stabilized basic monomers are provided. Said basic monomers are obtained by adding, to a basic monomer [e.g. an N,N-dialkylaminoalkyl (meth)acrylate or an N,N-dialkylaminoalkyl (meth)acrylamide], at least one member selected from the group consisting of amido group-containing compounds, phosphorous acid esters, phosphoric acid esters and phosphines and at least one phenol compound represented by the general formula:

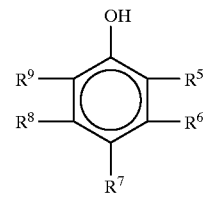

wherein $R^5$, $R^6$, $R^8$ and $R^9$ are each independently a hydrogen atom or an alkyl group having 1 to 4 carbon atoms; and $R^7$ is a hydrogen atom, an alkyl group having 1 to 4 carbon atoms or an alkoxy group having 1 to 4 carbon atoms. The color-stabilized basic monomers are more resistant to coloration when they are handled under such conditions that the oxygen concentration in the gas phase contacting therewith is 0.01 to 10% by volume.

20 Claims, No Drawings

COLOR-STABILIZED BASIC MONOMERS, PROCESS FOR PRODUCING THE SAME AND METHOD FOR HANDLING THE SAME

The present invention relates to color-stabilized basic monomers, a process for producing the same and a method for handling the same. More particularly, it relates to color-stabilized basic monomers low in coloration during handling (e.g. storage or transportation), specific examples of said basic monomers being N,N-dialkylaminoalkyl acrylates such as dimethylamino-ethyl acrylate (referred to hereinafter as DA in some cases) and the like; a process for producing the color-stabilized basic monomers; and a method for handling (e.g. storing or transporting) the same.

It is well-known that DA is used as a dye-ability-improver for fibers, an antistatic agent for plastics, a pigment-dispersing agent in coatings, an ultraviolet-curing coagent and the like and also used in the production of various polymers by homopolymerization or copolymerization with other copolymerizable monomers. However, DA is inferior in color stability and causes coloration easily in handling such as storage, transportation or the like, whereby the commercial value is greatly impaired.

A method for preventing such coloration of DA for stable storage or preservation thereof is proposed in Japanese Patent Application Laid-Open No. 144,521/1978, Japanese Patent Application Laid-Open No. 134,053/1992 and Japanese Patent Application Laid-Open No. 169,559/1992.

The method described in Japanese Patent Application Laid-Open No. 144,521/1978 comprises adding, to DA, phenothiazine alone or in combination with hydroquinone monomethyl ether or butylhydroxyanisole and storing the resulting mixture.

The method described in Japanese Patent Application Laid-Open No. 134,053/1992 comprises adding, to DA, hydroquinone monomethyl ether and storing the resulting mixture in the absence of oxygen.

The method described in Japanese Patent Application Laid-Open No. 169,559/1992 comprises storing an N,N-dialkylaminoalkyl acrylate such as DA or the like at a dissolved oxygen concentration of 0.5 to 10% (when oxygen is dissolved in the acrylate to saturation by blowing air into the acrylate, the dissolved oxygen concentration is indicated as 100%).

However, even when phenothiazine is added alone or in combination with hydroquinone monomethyl ether or butylhydroxyanisole, the coloration of DA is not prevented to a fully satisfactory level. When hydroquinone monomethyl ether is added to DA and the resulting mixture is stored in the absence of oxygen, polymerization of DA takes place in some cases.

Thus, an object of the present invention is to find a method for improving the color stability of basic monomers such as N,N-dialkylaminoalkyl acrylates and the like and provide thereby coloration-prevented (namely, color-stabilized) basic monomers, a process for producing the same and a method for handling the same.

The present inventors found out that when a specific additive is added to basic monomers, the coloration of the basic monomers can be prevented effectively and that when the handling (e.g. storage or transportation) of such color-stabilized basic monomers is effected in an atmosphere having a specific oxygen concentration, the coloration of the basic monomers can be prevented more effectively. The present invention has been completed based on the above knowledge.

Thus, according to the present invention, there is provided a color-stabilized basic monomer which, when subjected to a forced coloration test and measured for the L*, a* and b* of the L*a*b* color system, gives a ΔL* of 3 or less, a Δa* of 3 or less and a Δb* of 8 or less, the ΔL*, the Δa* and the Δb* being the differences of L*, a* and b* before and after said forced coloration test and being defined as follows:

ΔL*=|L* after test-L* before test| (absolute value),

Δa*=|a* after test-a* before test| (absolute value), and

Δb*=|b* after test-b* before test| (absolute value).

According to the present invention, there is also provided a process for producing a color-stabilized basic monomer which comprises adding, to a basic monomer, at least one member selected from the group consisting of amido group-containing compounds, phosphorous acid esters, phosphoric acid esters and phosphines and at least one phenol compound represented by the general formula (2):

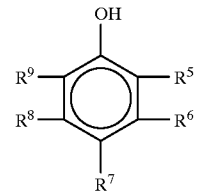

(2)

wherein $R^5$, $R^6$, $R^8$ and $R^9$ are each independently a hydrogen atom or an alkyl group having 1 to 4 carbon atoms, and $R^7$ is a hydrogen atom, an alkyl group having 1 to 4 carbon atoms or an alkoxy group having 1 to 4 carbon atoms.

According to the present invention, there is further provided a method for handling a color-stabilized basic monomer which comprises handling (e.g. storing or transporting) the color-stabilized basic monomer under such conditions that the oxygen concentration in the gas phase contacting therewith is 0.01 to 10% by volume.

The term "basic monomers" used herein means acrylate type monomers having terminal amino groups or terminal alkyl-substituted amino groups, and among them, monomers represented by the general formula (1) are particularly preferably used:

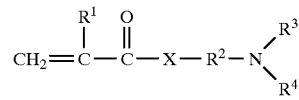

(1)

wherein $R^1$ is a hydrogen atom or a methyl group; $R^2$ is an alkylene group having 2 to 4 carbon atoms; $R^3$ and $R^4$ are each independently an alkyl group having 1 to 8 carbon atoms, preferably 1 to 4 carbon atoms; and X is —O— or —NH—.

Typical examples of the basic monomers represented by the above general formula (1) in which X is —O—[N,N-dialkylaminoalkyl (meth)acrylates], include N,N-dimethylaminoethyl (meth)acrylate, N,N-diethylaminoethyl (meth)acrylate, N,N-dipropylaminoethyl (meth)-acrylate, N,N-dimethylaminopropyl (meth)acrylate, N,N-diethyl-aminopropyl (meth)acrylate, N,N-dipropylaminopropyl (meth)acrylate, N,N-dibutylaminoethyl (meth)acrylate and N-methyl-N-ethylaminoethyl (meth)acrylate.

Typical examples of the basic monomers represented by the above general formula (1) in which X is —NH— [N,N-dialkylaminoalkyl (meth)acrylamides], include N,N-dimethylaminoethyl (meth)acrylamide, N,N-diethylaminoethyl (meth)acrylamide, N,N-dibutylaminoethyl (meth)acrylamide, N,N-dimethylaminopropyl (meth)acrylamide, N,N-diethylaminopropyl (meth)acrylamide and N,N-dimethylamino-3-methylbutyl (meth)acrylamide.

Incidentally, the term "(meth)acrylate" used above means acrylate or methacrylate and the term "(meth)acrylamide" used above means acrylamide or methacrylamide.

The color-stabilized basic monomers of the present invention are those basic monomers which, when subjected to a forced coloration test and measured for the L*, a* and b* of the L*a*b* color system, give a ΔL* of 3 or less, preferably 1.5 or less, more preferably 1 or less, a Δa* of 3 or less, preferably 1.5 or less, more preferably 1 or less, and a Δb* of 8 or less, preferably 3 or less, more preferably 1.5 or less, the ΔL*, the Δa* and the Δb* being the differences of L*, a* and b* before and after said forced coloration test and being defined as follows:

ΔL*=|L* after test-L* before test|
(absolute value),

Δa*=|a* after test-a* before test|
(absolute value), and

Δb*=|b* after test-b* before test|
(absolute value).

The forced coloration test method and the method for measuring the L*, a* and b* of the L*a*b* color system, both used in the present invention are as follows.

FORCED COLORATION TEST METHOD

In a 110-ml, stopperable glass vessel is placed 40 g of a basic monomer, the gas phase inside the vessel is filled with air, and the vessel is stoppered. Subsequently, this glass vessel is placed in a light-shilded, thermostatic chamber preset at 50° C. and then kept therein for 10 days.

METHOD FOR MEASURING L*, a* AND b*

Using a color difference meter of Model SZ-Σ80 manufactured by Nippon Denshoku Kogyo Co., Ltd., a basic monomer as a sample is placed in a cell having a thickness of 10 mm, and the L*, a* and b* thereof are measured under the conditions of light source C, 2° visual field and transmission mode. Incidentally, as a control, deionized water is used.

The above-mentioned color-stabilized basic monomers are obtained by adding, to the above-mentioned basic monomer, at least one member selected from the group consisting of amido group-containing compounds, phosphorous acid esters, phosphoric acid esters and phosphines and at least one phenol compound represented by the general formula (2):

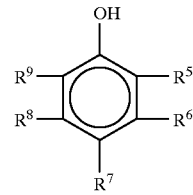

(2)

wherein $R^5$, $R^6$, $R^8$ and $R^9$ are each independently a hydrogen atom or an alkyl group having 1 to 4 carbon atoms, and $R^7$ is a hydrogen atom, an alkyl group having 1 to 4 carbon atoms or an alkoxy group having 1 to 4 carbon atoms.

Typical examples of the amido group-containing compounds, phosphorous acid esters, phosphoric acid esters, phosphines and phenol compounds of the general formula (2) used in the present invention are as follows.

AMIDO GROUP-CONTAINING COMPOUNDS

Oxamide derivatives

Compounds represented by the general formula:

R—NHCOCONH—R' wherein R and R' are each independently a hydrogen atom or a hydrocarbon group having 1 to 30 carbon atoms (for example, alkyl group, cycloalkyl group, aryl group and the like which may be substituted by a hydroxyl group, an alkoxy group or the like), which hydrocarbon group may be bonded to the nitrogen atom via any bonding group such as alkylene group, ether group, ester group, amido group or the like; for example, 2,2-oxamidobis[ethyl 3-(3,5-di-tert-butyl-4-hydroxyphenyl)propionate], oxalic acid bis (benzylidenehydrazide), N,N'-diphenyloxamide, N,N'-di(2-hydroxyphenyl)oxamide, 2-ethoxy-2'-ethyloxalic acid bisanilide, 2-ethoxy-5-tert-butyl-2'-ethyloxalic acid bisanilide, oxamide and oxamic hydrazide.

POLYBASIC ACID DERIVATIVES

Compounds represented by the general formula:

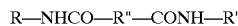

R—NHCO—R"—CONH—R' wherein R and R' are as defined above and R" is an alkylene group having 1 to 10 carbon atoms, a cyclo-alkylene group or an arylene group; for example, N,N'-tetramethylenebis(3, 5-di-tert-butyl-4-hydroxyphenyl-hydrocinnamide) and N,N'-hexamethylenebis(3,5-di-tert-butyl-4-hydroxy-hydrocinnamide).

OXAMIC ACID DERIVATIVES

Compounds represented by the general formula:

R-NHCOCOOR' wherein R and R' are as defined above; for example, oxamic acid, alkyl (having 1–8 carbon atoms) esters of oxamic acid, N-substituted oxamic acids and alkyl (having 1–8 carbon atoms) esters of N-substituted oxamic acids.

HYDRAZIDE DERIVATIVES

Compounds represented by the general formula:

R-CONHNH-R' wherein R and R' are as defined above; for example, N,N'-bis[3-(3,5-di-tert-butyl-4-hydroxyphenyl)propionyl] hydrazine, salicyloyl-N'-salicylidenehydrazine, dodecanedioic acid bis[2-(2-hydroxybenzoyl)hydrazide], isophthalic acid bis(2-phenoxypropionylhydrazide), N-salicyloyl-N'-aldehydohydrazine, N-salicyloyl-N'-acetyl-hydrazide, adipic acid dihydrazide, sebacic acid dihydrazide, dodecanedioic acid dihydrazide, isophthalic acid dihydrazide, maleic acid dihydrazide, 1,6-hexa-methylene-N,N'-dimethylsemicarbazide and 1,1,1',1'-tetramethyl-4,4'-(methylene-di-4-phenylene)disemicarbazide.

OTHERS

N-substituted acetamides such as acetanilide and the like; 3-(N-salicyloyl)amino-1,2,4-triazole; nylon 6,2; nylon 6,6; and polyamides.

Among the above-mentioned compounds, there are particularly preferably used 2,2-oxamidobis[ethyl 3-(3,5-di-tert-butyl-4-hydroxyphenyl)propionate], N,N'-hexamethylenebis(3,5-di-tert-butyl-4-hydroxy-hydrocinnamide), N,N'-bis[3-(3,5-di-tert-butyl-4-hydroxyphenyl)propionyl]hydrazine, 3-(N-salicyloyl)amino-1,2,4-triazole, dodecanedioic acid bis[2-(2-hydroxybenzoyl)-hydrazide], N-salicyloyl-N'-salicylidenehydrazine, oxalic acid bisbenzylidenehydrazide and isophthalic acid bis(2-phenoxypropionylhydrazide). Incidentally, these are compounds generally called (heavy) metal deactivators.

PHOSPHOROUS ACID ESTERS

Triphenyl phosphite, tris(nonylphenyl) phosphite, triethyl phosphite, tris(2-ethylhexyl) phosphite, tridecyl phosphite, tris(isodecyl) phosphite, tris(tridecyl) phosphite, diphenyl 2-ethylhexyl phosphite, diphenyl monodecyl phosphite, diphenyl mono(tridecyl) phosphite, diphenyl isodecyl phosphite, phenyl diisodecyl phosphite, phenyl di(tridecyl) phosphite, diphenyl isooctyl phosphite, diphenyl isodecyl phosphite, diphenyl tridecyl phosphite, [1,1-biphenyl-4,4'-diylbistetrakis(2,4-di-tert-butylphenyl)] ester of phosphonous acid [for example, IRGAFOS P-EPQFF (a trade name of CIBA GEIGY)], 4,4'-isopropylidenediphenyl alkyl phosphite [for example, MARK 1500 (a trade name of ADEKA CO., LTD.)], tris(mixed mono/di-nonylphenyl) phosphite [for example, MARK 239K (a trade name of ADEKA CO., LTD.)], tris(2,4-di-tert-butylphenyl) phosphite, tris (biphenyl) phosphite, distearyl pentaerythritol diphosphite, di(2,4-di-tert-butylphenyl) pentaerythritol diphosphite, di(2,4,6-tri-tert-butylphenyl) pentaerythritol diphosphite, di(nonylphenyl) pentaerythritol diphosphite, phenylbisphenol A-pentaerythritol diphosphite, tetratridecyl 4,4'-butylidene-bis(3-methyl-6-tert-butylphenol) diphosphite, hexatridecyl 1,1,3-tris(2-methyl-4-hydroxy-5-tert-butylphenyl)butane triphosphite, diethyl 3,5-di-tert-butyl-4-hydroxybenzylphosphite, dilauryl hydrogenphosphite, diphenyl hydrogenphosphite, tetraphenyl dipropylene glycol diphosphite, tetraphenyl tetra(tridecyl) pentaerythritol tetraphosphite, tetra(tridecyl) 4,4'-isopropylidenediphenyl diphosphite, trilauryl trithiophosphite, bis(tridecyl) pentaery-thritol diphosphite, bis(nonylphenyl) pentaerythritol diphosphite, tristearyl phosphite, distearyl pentaerythritol diphosphite, tris(2,4-di-tert-butylphenyl) phosphite, hydrogenated bisphenol A-pentaerythritol phosphite polymer [JPH-3800 (a trade name of Johoku Kagaku Kogyo K. K.)], hydrogenated bisphenol A phosphite polymer [HBP (a trade name of Johoku Kagaku Kogyo K. K.)], 9,10-dihydro-9xa-10-phosphophenanthrene-10-oxide, sodium bis(4-tert-butylphenyl)phosphate, sodium 2,2'-methylenebis(4,6-di-tert-butylphenyl)phosphate and 1,3-bis(diphenoxy-phosphonyloxy)benzene.

PHOSPHORIC ACID ESTERS

Ethyl diethylphosphonoacetate, ethyl acid phosphate [for example, JP-502 (a trade name)], butyl acid phosphate [for example, JP-504 (a trade name)], butyl pyrophosphate, butoxyethyl acid phosphate [for example, J-506 (a trade name)], 2-ethylhexyl acid phosphate [for example, J-508 (a trade name)], oleyl acid phosphate [for example, JP-518-0 (a trade name)], tetracosyl acid phosphate [for example, JP-524 (a trade name)], di(2-ethylhexyl) phosphate and ethylene glycol acid phosphate [for example, EGAP (a trade name)]. All the above trade names are of Johoku Kagaku Kogyo K. K..

PHOSPHINES

Trimethylphosphine, triethylphosphine, tripropylphosphine, tributylphosphine, trioctylphosphine, triphenylphosphine and tricyclohexylphosphine.

Among the above-mentioned phosphorous acid esters, phosphoric acid esters and phosphines (these are collectively called phosphorus-containing compounds in some cases), there are preferably used di(2,4,6-tri-tert-butylphenyl) pentaerythritol diphosphite, 9,10-dihydro-9xa-10-phosphophenanthrene-10-oxide, diphenyl hydrogenphosphite, di(2-ethylhexyl) phosphate and triphenylphosphine.

PHENOL COMPOUNDS OF GENERAL FORMULA (2)

Hydroquinone monomethyl ether, hydroquinone monoethyl ether, 2,6-di-tert-butylphenol, 2,4-di-tert-butylphenol, 2-tert-butyl-4-methoxyphenol, 2,4,6- trimethylphenol, 2,6-di-tert-butyl-4-ethylphenol, 2,4-dimethyl-6-tert-butylphenol, and 2,6-di-tert-butyl-4-hydroxytoluene 2,4,6-tri-tert-butylphenol.

The above-mentioned compounds are those which are generally called phenol type primary antioxidants, and among them, hydroquinone monomethyl ether is preferably used.

Accordingly, the above-mentioned color-stabilized basic monomers can be preferably prepared by adding, to the above-mentioned basic monomer, (1) at least one member selected from the group consisting of 2,2-oxamidobis[ethyl 3-(3,5-di-tert-butyl-4-hydroxy-phenyl)proprionate], N,N'-hexamethylenebis(3,5-di-tert-butyl-4-hydroxy-hydrocinnamide), N,N'-bis[3,5-di-tert-butyl-4-hydroxyphenyl)propionyl]hydrazine, 3-(N-salicyloyl) amino-1,2,4-triazole, dodecanedioic acid bis[2-(2-hydroxybenzoyl)hydrazide], N-salicyloyl-N'-salicylidene-hydrazide, oxalic acid bis(benzylidenehydrazide), isophthalic acid bis(2-phenoxypropionylhydrazide), (2,4,6-tri-tert-butylphenyl) pentaerythritol diphosphite, 9,10-dihydro-9xa-10-phosphophenanthrene-10-oxide, diphenyl hydrogenphosphite, di(2-ethylhexyl) phosphate and triphenylphosphine, and (2) hydroquinone monomethyl ether, in combination.

The above-mentioned color-stabilized basic monomers can be particularly preferably prepared by adding, to the above-mentioned basic monomer, (a) at least one member selected from the group consisting of 2,2-oxamidobis[ethyl 3-(3,5-di-tert-butyl-4-hydroxy-phenyl)propionate], N,N'-hexamethylenebis(3,5-di-tert-butyl-4-hydroxyhydrocinnamide), N,N'-bis[3,5-di-tert-butyl-4-hydroxyphenyl)propionyl]hydrazine, 3-(N-salicyloyl) amino-1,2,4-triazole, dodcanedioic acid bis[2-(2-hydroxybenzoyl)hydrazide], N-salicyloyl-N'-salicylidenehydrazide, oxalic acid bis (benzylidenehydrazide) and isophthalic acid bis(2-phenoxypropionylhydrazide), (b) at least one member selected from the group consisting of (2,4,6-tri-tert-butylphenyl) pentaerythritol diphosphite, 9,10-dihydro-9xa-10-phosphophenanthrene-10-oxide, oxide, diphenyl hydrogenphosphite, di(2-ethylhexyl) phosphate and triphenylphosphine, and (c) hydroquinone monomethyl ether, in combination.

The amount of the amido group-containing compound added (based on the weight of the basic monomer, the same applies hereinafter) is usually 0.0001 to 1% by weight, preferably 0.001 to 0.5% by weight. Each of the amounts of the phosphorous acid ester, phosphoric acid ester and phosphine added is usually 0.0001 to 1% by weight, preferably 0.001 to 0.5% by weight. The amount of the phenol compound of the general formula (2) added is usually 0.005 to 1% by weight, preferably 0.01 to 0.5% by weight.

The amount ratio of at least one member selected from the amido group-containing compounds and the phosphorus-containing compounds and at least one phenol compound represented by the general formula (2) is not critical, and can be appropriately determined within the above-mentioned amounts of individual compounds.

The color-stabilized basic monomers of the present invention cause no coloration even after long-term handling and are excellent in color stability. However, it is preferred to handle the color-stabilized basic monomers under such conditions that the oxygen concentration in the gas phase contacting therewith is 0.01 to 10% by volume, preferably 0.1 to 7% by volume. By handling under such conditions, the coloration of the basic monomers can be more effectively prevented. Incidentally, the term "handling" used herein means storage in a tank or the like; transportation by a tank lorry or the like; transfer through a piping including pipe, valve, nozzle and the like; and so forth.

Since the color-stabilized basic monomers of the present invention cause no coloration, for example, even after long-term storage, homopolymers thereof or copolymers thereof with other copolymerizable monomers are excellent in color characteristic and have a high commercial value.

The present invention is described below more specifically based on Examples.

Example 1

In an Oldershaw distillation apparatus (diameter: 35 mm, number of plates: 10, heating zone: glass flask having a volume of 2,000 ml) was placed 1,000 g of dimethylaminoethyl acrylate (DA) (manufactured by NIPPON SHOKUBAI Co., Ltd.). The pressure at the top of the distillation column was preset at 30 mmHg, and distillation was effected by heating the flask of the heating zone in an oil bath of 110° C. 500 g of a distillate obtained from the column top after 150 g had been distilled at a reflux ratio of 2 and at a column top temperature of 72 to 73° C., was used as a DA sample.

To 500 g of the above distillate were immediately ately added 1,000 ppm of hydroquinone monomethyl ether (MEHQ) as the phenol compound and 1,000 ppm of 2,2'-oxamidobis[ethyl 3-(3,5-di-tert-butyl-4-hydroxyphenyl)-propionate] [Naugard XL-1 (a trade name of Uniroyal Chemicals)].

The DA thus prepared was measured for L*, a* and b* according to the above-mentioned measurement method of the present invention. Subsequently, 40.0 g of this DA was weighed and placed in a 120 mm-high, 110 ml-vial with screw cap manufactured by MALUEM Co., Ltd. The vial was stoppered under an air atmosphere and subjected to the forced coloration test of the present invention. The L*, a* and b* of the DA after the test were measured and ΔL*, Δa* and Δb* were determined.

The results obtained are shown in Table 1. Incidentally, the DA after the above test was transparent, and the color number thereof (APHA) was 80. These are shown together in Table 1.

Examples 2 to 23

The same procedure as in Example 1 was repeated, except that the kinds and amounts of the additives were changed as shown in Table 1, whereby the ΔL*, Δa*, Δb*, transparency and color number of each DA were determined. The results obtained are shown in Table 1.

TABLE 1

|  | Example No. | | | | | |
|---|---|---|---|---|---|---|
|  | 1 | 2 | 3 | 4 | 5 | 6 |
| Amido group-containing compound | XL-1 | MD1024 | Irganox-1098 | IDH | — | — |
| Amount added (*) | 0.1 | 0.1 | 0.1 | 0.01 | — | — |
| Phosphorous-containing compound | — | — | — | — | PP-360 | PEP-36 |
| Amount added (*) | — | — | — | — | 0.1 | 0.1 |
| Phenol compound | MEHQ | MEHQ | MEHQ | MEHQ | MEHQ | MEHQ |
| Amount added (*) | 0.1 | 0.1 | 0.1 | 0.1 | 0.1 | 0.1 |
| DA after test |  |  |  |  |  |  |
| Transparency | Transparent | Transparent | Transparent | Transparent | Transparent | Transparent |
| APHA | 80 | 90 | 120 | 160 | 60 | 110 |
| Difference before and after test |  |  |  |  |  |  |
| ΔL* | 0.09 | 0.05 | 0.06 | 0.24 | 0.12 | 0.07 |
| Δa* | 0.92 | 1.04 | 1.26 | 1.61 | 0.65 | 1.32 |
| Δb* | 2.15 | 2.58 | 3.32 | 4.10 | 1.64 | 2.95 |

|  | Example No. | | | | | |
|---|---|---|---|---|---|---|
|  | 7 | 8 | 9 | 10 | 11 | 12 |
| Amido group-containing compound | — | — | XL-1 | XL-1 | MD1024 | XL-1 |
| Amount added (*) | — | — | 0.1 | 0.1 | 0.1 | 0.1 |

TABLE 1-continued

| | | | | | | |
|---|---|---|---|---|---|---|
| Phosphorous-containing compound | HCA | JP-260 | PP-360 | PP-360 | PP-360 | PEP-36 |
| Amount added (*) | 0.1 | 0.1 | 0.1 | 0.025 | 0.1 | 0.1 |
| Phenol compound | MEHQ | MEHQ | MEHQ | MEHQ | MEHQ | MEHQ |
| Amount added (*) | 0.1 | 0.1 | 0.1 | 0.1 | 0.1 | 0.1 |
| DA after test | | | | | | |
| Transparency | Transparent | Transparent | Transparent | Transparent | Transparent | Transparent |
| APHA | 240 | 200 | 10 | 20 | 10 | 50 |
| Difference before and after test | | | | | | |
| $\Delta L^*$ | 0.44 | 0.44 | 0.16 | 0.05 | 0.05 | 0.04 |
| $\Delta a^*$ | 2.49 | 1.91 | 0.15 | 0.35 | 0.16 | 0.58 |
| $\Delta b^*$ | 6.30 | 5.46 | 0.28 | 0.74 | 0.33 | 1.23 |

| | Example No. | | | | | |
|---|---|---|---|---|---|---|
| | 13 | 14 | 15 | 16 | 17 | 18 |
| Amido group-containing compound | MD1024 | — | XL-1 | XL-1 | XL-1 | XL-1 |
| Amount added (*) | 0.1 | — | 0.1 | 0.1 | 0.1 | 0.1 |
| Phosphorous-containing compound | PEP-36 | PP-360 | — | PP-360 | PEP-36 | HCA |
| Amount added (*) | 0.1 | 0.1 | — | 0.1 | 0.1 | 0.1 |
| Phenol compound | MEHQ | Topanol A | Topanol A | Topanol A | Topanol A | Topanol A |
| Amount added (*) | 0.1 | 0.1 | 0.1 | 0.1 | 0.1 | 0.1 |
| DA after test | | | | | | |
| Transparency | Transparent | Transparent | Transparent | Transparent | Transparent | Transparent |
| APHA | 30 | 50 | 110 | 40 | 170 | 80 |
| Difference before and after test | | | | | | |
| $\Delta L^*$ | 0.04 | 0.01 | 0.16 | 0.04 | 0.20 | 0.01 |
| $\Delta a^*$ | 0.46 | 0.62 | 1.24 | 0.42 | 2.01 | 1.01 |
| $\Delta b^*$ | 0.96 | 1.34 | 3.04 | 1.05 | 4.48 | 2.14 |

| | Example No. | | | | |
|---|---|---|---|---|---|
| | 19 | 20 | 21 | 22 | 23 |
| Amido group-containing compound | XL-1 | MD1024 | Irganox-1098 | CDA-1 | CUNOX |
| Amount added (*) | 0.1 | 0.1 | 0.1 | 0.1 | 0.025 |
| Phosphorous-containing compound | LB-58 | JP-260 | PEP-36 | PEP-36 | PEP-36 |
| Amount added (*) | 0.1 | 0.1 | 0.1 | 0.1 | 0.1 |
| Phenol compound | MEHQ | MEHQ | MEHQ | MEHQ | MEHQ |
| Amount added (*) | 0.1 | 0.1 | 0.1 | 0.1 | 0.1 |
| DA after test | | | | | |
| Transparency | Transparent | Transparent | Transparent | Transparent | Transparent |
| APHA | 70 | 35 | 30 | 140 | 250 |
| Difference before and after test | | | | | |
| $\Delta L^*$ | 0.01 | 0.07 | 0.13 | 0.20 | 0.32 |
| $\Delta a^*$ | 0.77 | 0.36 | 0.31 | 1.36 | 2.71 |
| $\Delta b^*$ | 1.81 | 0.92 | 0.86 | 3.84 | 6.90 |

Note:
(*): Weight % based on the weight of DA

Comparative Examples 1 to 6

The same procedure as in Example 1 was repeated, except that the kinds and amounts of the additives were changed as shown in Table 2, whereby the $\Delta L^*$, $\Delta a^*$, $\Delta b^*$, transparency and color number of each DA were determined. The results obtained are shown in Table 2.

TABLE 2

| | Comparative Example No. | | | | | | |
|---|---|---|---|---|---|---|---|
| | 1 | 2 | 3 | 4 | 5 | 6 | 7 |
| Amido group-containing compound | — | — | — | — | XL-1 | XL-1 | XL-1 |
| Amount added (*) | — | — | — | — | 0.1 | 0.1 | 0.1 |
| Phosphorous-containing compound | — | — | — | PEP-36 | PEP-36 | — | PEP-36 |
| Amount added (*) | — | — | — | 0.1 | 0.1 | — | 0.1 |
| Phenol compound | MEHQ | MEHQ | Irganox-245 | Irganox-245 | Irganox-245 | — | MEHQ |
| Amount added (*) | 0.01 | 0.1 | 0.1 | 0.1 | 0.1 | — | 0.1 |

TABLE 2-continued

| | Comparative Example No. | | | | | | |
|---|---|---|---|---|---|---|---|
| | 1 | 2 | 3 | 4 | 5 | 6 | 7 |
| DA after test | | | | | | | |
| Transparency | Hazy | Transparent | Transparent | Transparent | Transparent | Transparent | Hazy |
| APHA | 500< | 300 | 500< | 500< | 400 | 500< | 500< |
| Difference before and after test | | | | | | | |
| ΔL* | 7.15 | 0.70 | 2.88 | 5.35 | 0.64 | 3.35 | 7.15 |
| Δa* | 8.53 | 3.04 | 8.01 | 10.14 | 4.41 | 8.93 | 8.53 |
| Δb* | 51.99 | 8.35 | 26.91 | 47.60 | 10.68 | 32.72 | 51.99 |

Note:
(*): Weight % based on the weight of DA

Incidentally, in Tables 1 and 2, the meanings of the symbols used for the amido group-containing compound, phosphorus-containing compound and phenol compound are as follows.

Amido group-containing compound

XL-1 (Naugard XL-1 (a trade name of Uniroyal Chemicals): 2,2'-Oxamidobis[ethyl 3-(3,5-di-tert-butyl-4-hydroxyphenyl) propionate]

MD1024 (a trade name of CIBA GEIGY): N,N'-bis[3-(3,5-di-tert-butyl-4-hydroxyphenyl)propionyl]hydrazine Irganox-1098 (a trade name of CIBA GEIGY): N,N'-Hexam-ethylenebis(3,5-di-tert-butyl-4-hydroxyhydrocinnamide)

IDH: Isophthalic acid hydrazide

Phosohorus-containing compound

PP-360 (a trade name of K. I. Kasei K. K.): Triphenylphosphine

PEP-36 (a trade name of ASAHI DENKA KOGYO K. K.): 2,6-Di-tert-butyl-4-methylphenyl) pentaerythritol diphosphite HCA (a trade name of Sanko): 9,10-Dihydro-9xa-10-phosphophenanthrene-10-oxide JP-260 (a trade name of Johoku Kagaku K. K.): Diphenyl hydrogenphosphite LB-58 (a trade name of Johoku Kagaku K. K.): Di(2-ethylhexyl) phosphate

Phenol compound

MEHQ: Hydroquinone monomethyl ether

Topanol A (a trade name of ICI): 2,4-Dimethyl-6-tert-butylphenol

Irganox-245 (a trade name of CIBA GEIGY): Triethylene glycol bis[3-(3-tert-butyl-5-methyl-4-hydroxyphenyl)-propionate]

Irganox-1222 (a trade name of CIBA GEIGY): 3,5-Di-tert-butyl-4-hydroxybenzyl phosphonate diethyl ester From Comparative Examples 1 and 2, it is seen that when the phenol compound of the general formula (2) is added alone, no color-stabilized DA is obtained. From Comparative Examples 3, 4 and 5, it is seen that when other phenol compounds than those of the general formula (2) are used in combination with the phosphorus-containing compound or with the phosphorus-containing compound and the amido group-containing compound, no color-stabilized DA is obtained. Furthermore, from Comparative Examples 6 and 7, it is seen that even when the amido group-containing compound is added alone or in combination with the phosphorus-containing compound, no color-stabilized DA is obtained.

As proven by the Examples, the color-stabilized basic monomers of the present invention are excellent in color stability, cause no coloration and can be stably handled over a long period of time. Further, according to the present process, such color-stabilized basic monomers can be easily prepared. Furthermore, according to the present handling method, the coloration of the color-stabilized basic monomers can be more effectively prevented and the color stability can be long kept.

I claim:

1. A color-stabilized basic monomer which, when subjected to a forced coloration test and measured for the L*, a* and b* of the L*a*b* color system, gives a ΔL* of 3 or less, a Δa* of 3 or less and a Δb* of 8 or less, the ΔL*, the Δa* and the Δb* being the differences of L*, a* and b* before and after said forced coloration test and being defined as follows:

ΔL*=|L* after test-L* before test|
(absolute value),

Δa*=|a* after test-a* before test|
(absolute value), and

Δb*=|b* after test-b* before test|
(absolute value).

2. The basic monomer according to claim 1, wherein the ΔL*, the Δa* and the Δb* are 1.5 or less, 1.5 or less, and 3 or less, respectively.

3. The basic monomer according to claim 1, which is a compound represented by the following general formula:

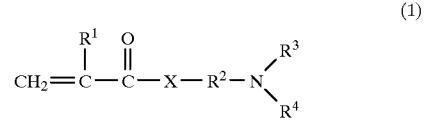

(1)

wherein $R^1$ is a hydrogen atom or a methyl group; $R^2$ is an alkylene group having 2 to 4 carbon atoms; $R^3$ and $R^4$ are each independently an alkyl group having 1 to 8 carbon atoms; and X is —O— or —NH—.

4. A process for producing a color-stabilized basic monomer, which comprises adding, to a basic monomer, at least one member selected from the group consisting of amido group-containing compounds, phosphorous acid esters, phosphoric acid esters and phosphines and at least one phenol compound represented by the general formula:

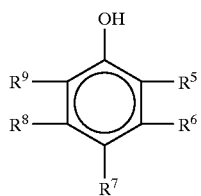

wherein $R^5$, $R^6$, $R^8$ and $R^9$ are each independently a hydrogen atom or an alkyl group having 1 to 4 carbon atoms; and $R^7$ is a hydrogen atom, an alkyl group having 1 to 4 carbon atoms or an alkoxy group having 1 to 4 carbon atoms.

5. The process of claim 4 for producing the color-stabilized basic monomer which comprises handling the color-stabilized basic monomer under such conditions that the oxygen concentration in the gas phase contacting therewith is 0.01 to 10% by volume.

6. A color-stabilized basic monomer represented by the formula:

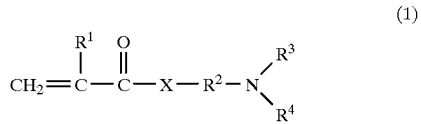

(1)

wherein $R^1$ is a hydrogen atom or a methyl group; $R^2$ is an alkylene group having 2 to 4 carbon atoms; $R^3$ and $R^4$ are each independently an alkyl group having 1 to 8 carbon atoms; and X is —O— or —NH— containing 0.001–0.5% based on the weight of said monomer of at least one additive which is a member selected from the group consisting of 2,2-oxamidobis(ethyl 3-(3,5-di-tert-butyl-4-hydroxyphenyl)propionate), N,N'-hexamethylenebis(3,5-di-tert-butyl-4-hydroxy-hydrocinnamide), N,N'-bis(3,5-di-tert-butyl-4-hydroxyphenyl)propionyl)hydrazine, 3-(N-salicyloyl)amino-1,2,4-triazole, dodecanedioic acid bis(2-(2-hydroxybenzoyl)hydrazide), N-salicyloyl-N'-salicylidenehydrazide, oxalic acid bis(benzylidenehydrazide), isophthalic acid bis(2-phenoxypropionylhydrazide), (2,4,6-tri-tert-butylphenyl) pentaerythritol diphosphite, 9,10-dihydro-9xa-10-phosphophenanthrene-10-oxide, diphenyl hydrogenphosphite, di(2-ethylhexyl) phosphate and triphenylphosphine, and 0.005–1.0% based on weight of said monomer of at least one phenol compound represented by the formula (2):

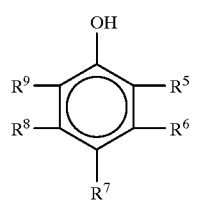

(2)

wherein $R^5$, $R^6$, $R^8$ and $R^9$ are each independently a hydrogen atom or an alkyl group having 1 to 4 carbon atoms, and $R^7$ is a hydrogen atom, an alkyl group having 1 to 4 carbon atoms or an alkoxy group having 1 to 4 carbon atoms, wherein said color-stabilized basic monomer when subjected to a forced coloration test is transparent and has a coloration number (APHA) of 250 or less.

7. The color-stabilized basic monomer of claim 6, wherein said phenol compound is at least one member selected from the group consisting of hydroquinone monomethyl ether, hydroquinone monoethyl ether, 2,6-di-tert-butylphenol, 2,4-di-tert-butylphenol, 2-tert-butyl-4-methoxyphenol, 2,4,6-trimethylphenol, 2,6-di-tert-butyl-4-ethylphenol, 2,4-dimethyl-6-tert-butylphenol, 2,6-di-tert-butyl-4-hydroxytoluene and 2,4,6-tri-tert-butylphenol.

8. The color-stabilized basic monomer of claim 6, wherein said additive is (a) at least one member selected from the group consisting of 2,2-oxamidobis(ethyl 3-(3,5-di-tert-butyl-4-hydroxyphenyl)propionate), N,N'-hexamethylenebis(3,5-di-tert-butyl-4-hydroxy-hydrocinnamide), N,N'-bis(3,5-di-tert-butyl-4-hydroxyphenyl)propionyl)hydrazine, 3-(N-salicyloyl)amino-1,2,4-triazole, dodcanedioic acid bis(2-(2-hydroxybenzoyl)hydrazide), N-salicyloyl-N'-salicylidenehydrazide, oxalic acid bis(benzylidene-hydrazide) and isophthalic acid bis(2-phenoxypropionyl-hydrazide; and (b) at least one member selected from the group consisting of (2,4,6-tri-tert-butylphenyl) pentaerythritol diphosphite, 9,10-dihydro-9xa-10-phosphophenanthrene-10-oxide, diphenyl hydrogenphosphite, di(2-ethylhexyl) phosphate and triphenylphosphine.

9. A color-stabilized basic monomer represented by the formula:

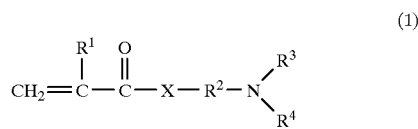

(1)

wherein $R^1$ is a hydrogen atom or a methyl group; $R^2$ is an alkylene group having 2 to 4 carbon atoms; $R^3$ and $R^4$ are each independently an alkyl group having 1 to 8 carbon atoms; and X is —O— or —NH— containing 0.001–0.5% based on the weight of said monomer of at least one additive which is a member selected from the group consisting of 2,2'-oxamidobis(ethyl 3-(3,5-di-tert-butyl-4-hydroxyphenyl)propionate), N,N'-bis(3-(3,5-di-tert-butyl-4-hydroxyphenyl)propionyl)hydrazine, N,N'-hexamethylenebis(3,5-di-tert-butyl-4-hydroxy-hydrocinnamide), isophthalic acid hydrazide, triphenyl-phosphine, 2,6-di-tert-butyl-4-methylphenyl) pentaerythritol diphosphite, 9,10-dihydro-9xa-10- phosphophenanthrene-10-oxide, diphenyl hydrogenphosphite and di-(2-ethylhexyl) phosphate, and 0.005–1.0% based on weight of said monomer of at least one phenol compound which is a member selected from the group consisting of hydroquinone monomethyl ester, hydroquinone monoethyl ether, 2,6-di-tert-butylphenol, 2,4-tert-butylphenol, 2-tert-butyl-4-methoxyphenol, 2,4,6-trimethylphenol, 2,6-di-tert-butyl-4-ethylphenol, 2,4-dimethyl-6-tert-butylphenol, 2,6-di-tert-butyl-4-hydroxytoluene and 2,4, 6-tri-tert-butylphenol, and wherein said color-stabilized basic monomer when subjected to a forced coloration test is transparent and has a coloration number (APHA) of 250 or less.

10. The color-stabilized basic monomer of claim 9, wherein said additive is (a) at least one member selected from the group consisting of 2,2'-oxamidobis(ethyl 3-(3,5-di-tert-butyl-4-hydroxyphenyl)propionate), N,N'-bis(3-(3,5-di-tert-butyl-4-hydroxyphenyl)propionyl)hydrazine, N,N'-hexamethylenebis(3,5-di-tert-butyl-4-hydroxyhydrocinnamide), isophthalic acid hydrazide and (b) at least one member selected from the group consisting of triphenyl-phosphine, 2,6-di-tert-butyl-4-methylphenyl) pentaerythritol diphosphite, 9,10-dihydro-9xa-10-phosphophenanthrene-10-oxide, diphenyl hydrogenphosphite, and di(2-ethylhexyl) phosphate.

11. The color-stabilizer of claim 9, wherein said phenol compound is at least one of hydroquinone monomethyl ether and 2,4-dimethyl-6-tert-butylphenol.

12. A process for producing a color-stabilized basic monomer, which comprises adding, to a basic monomer of the formula:

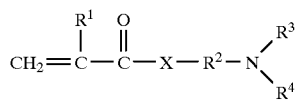 (1)

wherein $R^1$ is a hydrogen atom or a methyl group; $R^2$ is an alkylene group having 2 to 4 carbon atoms; $R^3$ and $R^4$ are each independently an alkyl group having 1 to 8 carbon atoms; and X is —O— or —NH—, 0.001 to 0.5% based on the weight of said monomer of at least one additive which is a member selected from the group consisting of amido group-containing compounds, phosphorus acid esters, phosphoric acid esters and phosphines, and 0.005 to 1.0% based on the weight of said monomer of at least one phenol compound represented by the formula:

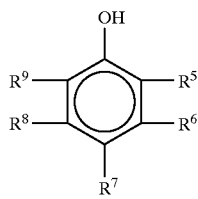

wherein $R^5$, $R^6$, $R^8$ and $R^9$ are each independently a hydrogen atom or an alkyl group having 1 to 4 carbon atoms; and $R^7$ is a hydrogen atom, an alkyl group having 1 to 4 carbon atoms or an alkoxy group having 1 to 4 carbon atoms.

13. The process of claim 12, wherein said color-stabilized basic monomer when subjected to a forced coloration test is transparent and has a coloration number (APHA) of 250 or less.

14. The process of claim 12, wherein said additive is at least one member selected from the group consisting of 2,2-oxamidobis(ethyl 3-(3,5-di-tert-butyl-4-hydroxy-phenyl)propionate), N,N'-hexamethylenebis(3,5-di-tert-butyl-4-hydroxy-hydrocinnamide), N,N'-bis(3,5-di-tert-butyl-4-hydroxy-phenyl)propionyl)hydrazine, 3-(N-salicyloyl)amino-1,2,4-triazole, dodecanedioic acid bis(2-(2-hydroxybenzoyl)hydrazide), N-salicyloyl-N'-salicylidene-hydrazide, oxalic acid bis)benzylidenehydrazide), isophthalic acid bis (2-phenoxypropionylhydrazide), (2,4,6-tri-tert-butylphenyl) pentaerythritol diphosphite, 9,10-dihydro-9xa-10-phosphophenanthrene-10-oxide, diphenyl hydrogenphosphite, di(2-ethylhexyl) phosphate and triphenylphosphine.

15. The process of claim 12 wherein said phenol compound is at least one member selected from the group consisting of hydroquinone monomethyl ether, hydroquinone monoethyl ether, 2,6-di-tert-butylphenol, 2,4-di-tert-butylphenol, 2-tert-butyl-4-methoxyphenol, 2,4,6-trimethylphenol, 2-6-di-tert-butyl-4-ethylphenol, 2,4-dimethyl-6-tert-butylphenol, 2-6-di-tert-butyl-4-hydroxytoluene and 2,4,6-tri-tert-butylphenol.

16. The process of claim 12, wherein said additive is (a) at least one member selected from the group consisting of 2,2-oxamidobis(ethyl 3-(3,5-di-tert-butyl-4-hydroxyphenyl)propionate), N,N'-hexamethylenebis(3,5-di-tert-butyl-4-hydroxy-hydrocinnamide), N,N'-bis(3,5-di-tert-butyl-4-hydroxyphenyl)propionyl)hydrazine, 3-(N-salicyloyl)amino-1,2,4-triazole, dodcanedioic acid bis(2-(2-hydroxybenzoyl)hydrazide), N-salicyloyl-N'-salicylidenehydrazide, oxalic acid bis(benzylidene-hydrazide) and isophthalic acid bis(2-phenoxypropionyl-hydrazide), and (b) at least one member selected from the group consisting of (2,4,6-tri-tert-butylphenyl) pentaerythritol diphosphite, 9,10-dihydro-9xa-10-phosphophenanthrene-10-oxide, diphenyl hydrogenphosphite, di(2-ethylhexyl) phosphate and triphenylphosphine.

17. A process for producing a color-stabilized basic monomer, which comprises adding, to a basic monomer of the formula:

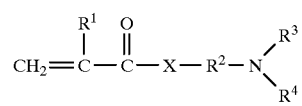 (1)

wherein $R^1$ is a hydrogen atom or a methyl group; $R^2$ is an alkylene group having 2 to 4 carbon atoms; $R^3$ and $R^4$ are each independently an alkyl group having 1 to 8 carbon atoms; and X is —O— or —NH—, 0.001 to 0.5% based on the weight of said monomer at least one additive which is a member selected from the group consisting of 2,2'-oxamidobis(ethyl 3-(3,5-di-tert-butyl-4-hydroxyphenyl) propionate), N,N'-bis(3-(3,5-di-tert-butyl-4-hydroxy-phenyl)propionyl)hydrazine, N,N'-hexamethylenebis(3,5-di-tert-butyl-4-hydroxy-hydrocinnamide), isophthalic acid hydrazide, triphenylphosphine, 2,6-di-tert-butyl-4-methylphenyl) pentaerythritol diphosphite, 9,10-dihydro-9xa-10-phosphophenanthrene-10-oxide, diphenyl hydrogenphosphite, di(2-ethylhexyl) phosphate, and 0.005–1.0% based on weight of said monomer of at least one phenol compound which is a member selected from the group consisting of hydroquinone monomethyl ether, hydroquinone monoethyl ether, 2,6-di-tert-butylphenol, 2,4-di-tert-butylphenol, 2-tert-butyl-4-methoxyphenol, 2,4,6-trimethylphenol, 2,6-di-tert-butyl-4-ethylphenol, 2,4-dimethyl-6-tert-butylphenol, 2,6-di-tert-butyl-4-hydroxytoluene and 2,4,6-tri-tert-butylphenol, and wherein said color-stabilized basic monomer when subjected to a forced coloration test is transparent and has a coloration number (APHA) of 250 or less.

18. The process of claim 17, wherein said additive is (a) at least one member selected from the group consisting of 2,2'-oxamidobis(ethyl 3-(3,5-di-tert-butyl-4-hydroxyphenyl)propionate), N,N'-bis(3-(3,5-di-tert-butyl-4-hydroxyphenyl)propionyl)hydrazine, N,N'-hexamethylenebis(3,5-di-tert-butyl-4-hydroxy-hydrocinnamide), isophthalic acid hydrazide and (b) at least one member selected from the group consisting of triphenyl-phosphine, 2,6-di-tert-butyl-4-methylphenyl) pentaerythritol diphosphite, 9,10-dihydro-9xa-10-phosphophenanthrene-10-oxide, diphenyl hydrogenphosphite, and di(2-ethylhexyl) phosphate.

19. The process of claim 17, wherein said phenol compound is at least one of hydroquinone monomethyl ether and 2,4-dimethyl-6-tert-butylphenol.

20. The process of claim 17, wherein the color-stabilized basic monomer is handled under conditions such that the oxygen concentration in a gas contacting the basic monomer is 0.01 to 10% by volume.

* * * * *